(12) United States Patent
Ferrando

(10) Patent No.: US 9,028,955 B1
(45) Date of Patent: May 12, 2015

(54) ION-PERMEABLE MEMBRANE FOR ELECTROCHEMICAL CELL

(75) Inventor: William A. Ferrando, Arlington, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1413 days.

(21) Appl. No.: 12/571,459

(22) Filed: Oct. 1, 2009

(51) Int. Cl.
*H01M 2/16* (2006.01)
*H01M 4/36* (2006.01)
*H01M 4/1399* (2010.01)
*G01N 27/40* (2006.01)
*H01M 4/66* (2006.01)

(52) U.S. Cl.
CPC .............. *H01M 2/1653* (2013.01); *H01M 4/36* (2013.01); *H01M 4/1399* (2013.01); *G01N 27/40* (2013.01); *H01M 4/66* (2013.01); *Y10T 428/26* (2015.01)

(58) Field of Classification Search
CPC ... H01M 2/1653; H01M 4/1399; H01M 4/66; H01M 4/36; G01N 27/40; Y10T 428/26
USPC .......... 428/220; 429/129, 135, 137, 142, 145, 429/122, 126, 247, 249, 250, 254, 309, 317
See application file for complete search history.

(56) References Cited

U.S. PATENT DOCUMENTS

| | | | |
|---|---|---|---|
| 3,427,206 A * | 2/1969 | Sears et al. | 429/144 |
| 4,797,190 A | 1/1989 | Peck | |
| 5,283,138 A | 2/1994 | Ferrando | |
| 7,070,882 B1 * | 7/2006 | Ferrando | 429/218.1 |
| 2007/0141463 A1 * | 6/2007 | Stevanovic | 429/217 |

OTHER PUBLICATIONS

William A. Ferrando, Development of a novel composite anode, Journal of Power Sources, 130 (2004) 309-314.
Lubrizol Pharmaceutical Bulletin 5, Neutralization Procedures, pp. 1-5, Oct. 29, 2008.

* cited by examiner

*Primary Examiner* — Maria Veronica Ewald
*Assistant Examiner* — Nancy Johnson
(74) *Attorney, Agent, or Firm* — Richard A. Morgan

(57) ABSTRACT

An electrochemical cell comprises an ion permeable, liquid and vapor impermeable, membrane made by a solvent casting process. Two mutually insoluble polymers are cast together with the aide of mutually soluble co-solvents. The ion permeable membrane comprises a high molecular weight polyisobutylene polymer structural component. The linearized poly(acrylic acid) polymer ion conducting component comprises which is 4 wt % to 6 wt % of the membrane. The dried ion permeable membrane has a thickness of about 0.1 millimeters. The membrane is hydrated and used for transporting ions in an electrochemical cell. The cell demonstrates good reversibility, i.e. rechargability.

20 Claims, 1 Drawing Sheet

ION-PERMEABLE MEMBRANE FOR ELECTROCHEMICAL CELL

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The invention relates to an ion permeable membrane made by a method. More particularly, the invention relates to an electrochemical cell including the ion permeable membrane.

2. Discussion of the Related Art

Polymeric, non-porous, membranes are typically thin films comprising amorphous phases of structural molecules comprising long chain polymers. These membranes are impermeable to liquids and vapors. Polymeric membranes can be made to have permeability to specific groups of ions such as anions or cations. In general, the selectivity of an ion permeable membrane is based on specific physical limitations imparted to the membrane by its structure. Certain long chain polymers having the ability to transport ions along their length are referred to in the art as pores. Selectivity may result from the long polymer chains containing isolated charges along the length of the chain. These charges may be provided by ion exchange monomers. In polymers including these monomers, the active charge ion exchange radicals are distanced from each other resulting in isolated charges along the chain. The distance between the charge sites allows transport of only selected ions along the polymer chain.

Lithium ion cells are known for a high energy density. However, their manufacturing cost is relatively high due to special fabrication requirements. In addition, the presence of reactive lithium and flammable electrolyte can be dangerous in some environments where the cells might be used.

There remains a need in the art for an improved ion permeable membrane for a electrochemical cell. Problems found in the prior art are solved, at least in part, by the method for an electrochemical cell with the ion permeable membrane of the invention.

SUMMARY OF THE INVENTION

An electrochemical cell comprises an ion permeable, liquid and gas impermeable, membrane made by a method. The ion permeable membrane comprises a structural component of high molecular weight polyisobutylene and an ion conducting component of poly(acrylic acid).

According to the method: (a.) High molecular weight polyisobutylene is dissolved in a dry first solvent to produce a first solution. (b.) Poly(acrylic acid) having a specified molecular weight is dissolved in a dry second solvent and neutralized to form a second solution. (c.) The two solutions are mixed to form a solution mixture having an advantageous concentration of 4 wt % to 6 wt % poly(acrylic acid) basis polymer in the solution mixture. (d.) The solution mixture is cast on a casting surface. The first solvent and second solvent are removed. (e.) An ion permeable, liquid and gas impermeable, membrane having a thickness of 0.1 mm or greater is formed.

The ion permeable membrane is particularly useful for separating two electrolytes and transporting ions in an electrochemical cell.

DETAILED DESCRIPTION OF THE INVENTION

Figure 1:
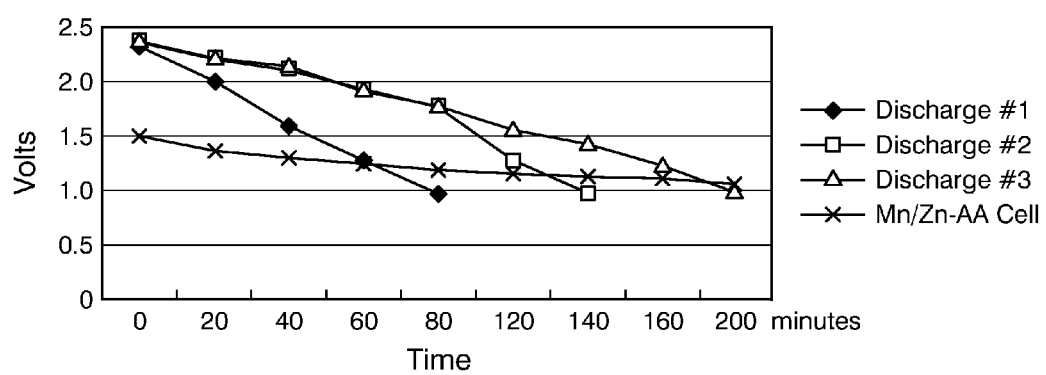
FIG. 1 is a plot of data demonstrating a Mn/Zn cell of the invention by way of three successive voltage discharges with respect to time in comparison with the first discharge of a rechargeable commercial Mn/Zn cell.

The electrochemical cell relies on an ion permeable, liquid and vapor impermeable membrane. The membrane comprises a relatively inert, structural component and a relatively active, ion transporting component. The inert, structural component supports and electrostatically isolates each active, ion transporting component.

The structural component comprises high molecular weight polyisobutylene comprising polymerized isobutylene monomer. Each monomer unit has a molecular weight of 56.11 grams/mole. The polymer is prepared by cationic polymerization, typically with the aide of boron trifluoride catalyst. To achieve the desired high molecular weights, polymerization is carried out at reduced reaction temperature to prevent side reactions. Under these conditions a polymer is produced having a number average molecular weight in excess of 1 million. The number average molecular weight range for the structural component of the invention is about 80,000 to about 1,000,000, preferably about 100,000 to about 1,000,000. Polymer in this molecular weight range is commercially available in powder form.

The structural component of the membrane is essentially the polymer polyisobutylene. This polymer is chosen to provide a strong, flexible and chemically durable membrane that is impermeable to liquid and vapor. It is known that isobutylene can be polymerized with other compatible monomers to produce high molecular weight copolymers. This could be done with the intent of adding stiffness to the membrane. However, it is also known that relatively small amounts of other monomers can significantly alter the physical properties of the membrane product. The structural component functions to space and insulate the poly(acrylic acid) component. In addition, it imparts liquid and vapor impermeability to the membrane. Polyisobutylene does not hydrate in contrast to poly(acrylic acid) which does hydrate. Likewise, any copolymer added to the polyisobutylene must not hydrate. A hydrated inert support structure would not isolate and insulate the poly(acrylic acid) active component. This is essential for ion transport. Any copolymer added to the high molecular weight polyisobutylene structural support component must be carefully evaluated in view of the physical and chemical properties it imparts to the membrane.

The polyisobutylene is weighed out and dissolved in a first solvent. Techniques are known in the art to facilitate dissolving high molecular weight polyisobutylene in a solvent. It may be necessary to allow time for the polymer to fully dissolve. For example, samples have been stirred overnight to dissolve the polymer. If necessary the solution can be filtered to remove any residual undissolved polyisobutylene polymer or any debris.

The first solvent is selected from the group of solvents that readily dissolve polyisobutylene and are soluble in the second solvent. That is, the first solvent and the second solvent are co-solvents. Tetrahydrofuran (THF) and dichloro methane are suitable first solvents with THF being preferred. Other first solvents include benzene, toluene, ethylbenzene, cycloexane, n-heptane, methyl ethyl ketone (MEK) and chlorinated hydrocarbons such as chloro-benzene, carbon tetrachloride and tetrachloroethylene. The first solvent must be dry, i.e free of water.

The active, ion transporting component is poly(acrylic acid) comprising polymerized acrylic acid monomer. Each monomer has a molecular weight of 60.05 grams/mole. The molecular weight of the polymer is about 100,000 to about 4 million, preferably about 1.2 million to about 4 million. Linearized polymer in the lower molecular weight range provides conductivity through a membrane by cross-linking. The higher molecular weight polymers are able to provide direct conductivity through a membrane along a single polymer chain. For this reason, the molecular weight range of about 1.2 million to about 4 million is preferred. This material is available in pellet form under the trade name CARBOPOL®. The material is weighed out and dissolved in a second solvent. If necessary the dissolved poly(acrylic acid) can be filtered to remove any undissolved monomer or other debris.

The second solvent is selected from the group of solvents that dissolve poly(acrylic acid) and are soluble in the first solvent. These solvents include alcohols that are liquid at room temperature such as methyl alcohol, ethyl alcohol, propyl alcohol, isopropyl alcohol, butyl alcohol, and isobutyl alcohol. Ethyl alcohol is preferred. In the examples the preferred solvent pairing is tetrahydrofuran (THF) as a first solvent and ethyl alcohol as a second solvent. The second solvent must be dry, i.e. free of water.

In solution, the dissolved poly(acrylic acid) is tightly-coiled along the polymer chain. The polymer uncoils slightly when dissolved in solvent. Neutralization of the polymer uncoils or linearizes it, extending it to the full length. The polymer is neutralized in solvent by addition of an appropriate long chain amine. Examples of suitable long chain amines include diisopropanol amine, polyoxyethylene (15) coconut alkylamine and triethanolamine.

Neutralization ionizes the poly(acrylic acid) polymer, generating negative charges along the polymer chain. Repulsions between these negative charges cause the chain to extend to its full length. A rough calculation was made to determine the length of the linearized poly(acrylic acid). For this calculation, the assumption was made that all monomers lie along the polymer backbone. A carbon ion radius of $0.15 \times 10^{-8}$ centimeters was taken from the literature. A linearized 1,200,000 molecular weight molecule containing $10^5$ carbon atoms was calculated to have a length of 0.01 centimeters (0.1 millimeters). This compared well with the measured thickness of the membrane in Example 1a. It is understood that there is cross-linking between and among nominally linearized poly(acrylic acid) polymers. According, the cross-linking provides conductivity between poly(acrylic acid) polymers through membranes that are thicker than the length of any single poly(acrylic acid) polymer chain. It is preferred that ion permeability from one face of the membrane to the other face of the membrane be provided along a single linearized poly(acrylic acid) polymer chain.

The first polymer solution and the second polymer solution are combined in an amount such that the poly(acrylic acid) comprises about 4 wt % to about 6 wt % of the solution based on the polymers in the solution mixture. The solution is thoroughly mixed and has a Brookfield viscosity of about 5 centipoise (cp) to about 1000 centipoise (cp). The co-solvents, i.e. first solvent and the second solvent, are the reason for the compatibility of the two otherwise incompatible polymers. The viscosity of the solution is adjusted to control the thickness of the product membrane. That is, more or less of the solvents are added to achieve the desired membrane thickness after removal of the co-solvents.

The resulting solution is filtered if necessary and degassed if necessary to remove any inclusions that could produce holes in the membrane. The solution is than cast on a casting surface. Then solvent is removed by conventional methods such as by exposure to dry air at moderate temperatures and application of slight vacuum to free the membrane casting of solvent, referred to in the art as drying.

A process for solvent casting comprises casting a solvent mixture comprising two mutually soluble solvents, i.e. co-solvents, with polyisobutylene polymer dissolved in one solvent and neutralized poly(acrylic acid) polymer dissolved in the other solvent. The dry co-solvent mixture is thoroughly mixed and filtered to remove any undissolved polymer, debris or bubbles that might cause holes in the membrane product. The filtered liquid is passed from the mixing vessel onto a casting support surface. The casting surface may be stationary or a moving casting belt. The cast material is freed of solvent on the casting surface by solvent evaporation.

The thickness of the membrane is controlled by adjusting the viscosity of the solution of co-solvents and polymers and also the thickness of the liquid layer laid down on the casting surface. Both are adjusted with experience to yield a membrane of the desired thickness. In general the amount of poly(acrylic acid) is about 4 wt % to about 6 wt % of the total amount of polymer and can be adjusted in this range. By default the amount of solvent is the primary variable in controlling viscosity.

Criticality has been found in the relative amount of poly(acrylic acid) relative to the polyisobutylene. Liquid and vapor impermeable membranes with greater than about 6 wt poly(acrylic acid) could not be successfully fabricated. Holes formed in the cast film during solvent removal on the casting surface. The resulting membrane could not be pulled off the casting surface in a single piece. The pieces that came off the casting surface were not strong enough to stretch. The preferred upper end limit for poly(acrylic acid) is 5.7 wt %, more preferably 5 wt % poly(acrylic acid).

At the lower end of the range, it was estimated that membranes with less than about 4 wt % poly(acrylic acid) would not have enough conductivity to make them useful in an electrochemical cell. In addition, with the relatively low amount of poly(acrylic acid), a hydrated membrane has relatively few charge sites for ion conduction. Poly(acrylic acid) is used in the art to form hydrogels. However, a hydrogel would not function as a membrane to transmit ions while simultaneously preventing transmission of liquid and vapor. Nor is a hydrogel capable of providing structural support. Polyisobutylene in the membrane does not hydrate. The polyisobutylene isolates and insulates hydrated poly(acrylic acid) as well as providing structural support. The individual poly(acrylic acid) molecules hydrate without hydrating the entire membrane to form a hydrogel. Hydrogels are specifically excluded from the invention. A hydrogel does not have the requisite strength to function in applications of the invention.

The required membrane thickness is determined by the length of the poly(acrylic acid) polymer. As shown above, the length of poly(acrylic acid) polymer chains is calculable. It is preferred that the ends of each polymer molecule be exposed to the two electrolyte solutions. The thickness of the membrane is selected, in view of the poly(acrylic acid) polymer length to accomplish this. Membrane thickness of 0.1 millimeters to 0.4 millimeters (3.937 mils to 15.748 mils) is typical.

The drying temperature is usually set lower than the casting temperature. For example, if the casting temperature is 40° C.

the drying temperature is set at 20° C. to 30° C. But these values are an initial suggestion from which adjustments are expected and are not intended to be limiting.

Solvent is evaporated from the membrane by exposure to the atmosphere. Evaporation rate can be increased by blowing with dry air and with the application of a slight vacuum. The solvent-free membrane is stripped off the casting surface and may be subject to additional evaporation to remove any residual solvent. The membrane is visually inspected for holes, non-uniformity and subjected to quality control measurements. The membrane is then stored in a clean, dry atmosphere prior to use.

Quality control measurements include standard tests performed to measure the physical properties of thin films. Total Elongation is measured according to procedures known in the art, for example in an Instron Tensile Testing Machine. Tensile Strength is measured according to ASTM D882-67, Tensile Properties of Thin Plastic Sheeting. Tear Resistance is measured according to ASTM D 1938-67, Tear Propagation or Resistance to in Plastic Film and Sheeting by Single Tear Method.

The solvent free, dry membrane is strong and durable. Immediately before use it is hydrated to attach water molecules to the poly(acrylic acid) chains. This is carried out by contacting with water or aqueous electrolyte fluids. The linearized poly(acrylic acid) is a long chain polymer molecule which adsorbs and immobilizes aqueous electrolyte molecules along its length. Ions are transported along the poly(acrylic acid) polymer chain via the water molecules. Each poly(acrylic acid) molecule is isolated so that the ions travel along the polymer chain and not substantially between adjacent polymer chains. In an electrochemical cell, the anode operates with the movement of $OH^-$ ions along the polymer chain while current is drawn from the cell. However, the major portion of the membrane is polyisobutylene polymer which does not hydrate. The membrane is not a hydrogel.

The membranes are useful in batteries, fuel cells, ion separators, electrochemical electrolyzer cells to crack water and the like and in equivalent ion permeable membrane uses.

This invention is shown by way of Example.

EXAMPLE 1a

A polymer membrane was synthesized according to the invention. High molecular weight polyisobutylene (Aldrich Chemical Co., Milwaukee, Wis.) was weighed out in an amount of 5 grams and dissolved in about 100 milliliters of dry tetrahydrofuran (THF) at about 40° C.

In a second vessel, 0.2 grams of poly(acrylic acid) having a molecular weight of 1,200,000 (Carbopol® 980, Lubrizol Advanced Materials, Inc., Cleveland Ohio 44141) was dissolved in about 100 milliliters of dry ethanol. The poly(acrylic acid) was in the form of a fine powder, each particle of which was a single polymer molecule. The poly(acrylic acid) solution was neutralized with the addition of dry Ethomeen C/15, an ethylene oxide condensate of a cocoalkylamine containing 5 moles of ethylene oxide (AKZO Engineering Plastic, Inc., Chicago, Ill.). The neutralization procedure was done in the absence of water according to Pharmaceutical Bulletin 5 Neutralization Procedures, Lubrizol Advanced Materials, Inc., Cleveland, Ohio.

The neutralized (linearized) poly(acrylic acid) was added slowly to the polyisobutylene solution to produce a uniform admixture.

A clean glass casting plate was prepared by brushing with a thin coating of mineral oil. The admixture was poured evenly over the casting plate surface at room temperature. The solvent evaporated at room temperature and atmospheric pressure and formed a uniform film. The polymer film was allowed to dry overnight and then carefully removed from the casting plate by hand. The film was visually inspected for uniformity and the thickness measured 0.004 inches (0.1016 millimeters).

The length of the poly(acrylic acid) polymer chain was calculated. A linearized molecule containing $10^5$ carbon atoms has a length of 0.01 centimeters (0.1 millimeters). This corresponds with the measured thickness of the membrane in this example.

EXAMPLE 1b

An optical micrograph of a membrane according to the invention was made. The micrograph showed ends of the poly(acrylic acid) molecules at the membrane surface.

This was taken as confirmation that the poly(acrylic acid) molecules extended entirely through the thickness of the membrane.

No points of light were observed in the micrograph. Given the scale of the optical micrograph, micron size and submicron size holes in the membrane would have been identifiable as points of light.

It was concluded that there were no micron size or submicron size holes in the membrane.

EXAMPLE 1c

An electrochemical cell was made according to the invention. Two half cell cavities separated by the membrane of Example 1a were clamped together. One cell cavity contained a positive $PbO_2$ electrode taken from a small commercial lead-acid battery for use as the cathode. The other cell cavity contained a zinc electrode taken from a silver-zinc cell for use as the anode. The electrode dimensions were about 4.5 centimeters×6.5 centimeters.

The membrane was hydrated with the addition of aqueous electrolyte to the half cells. The cathode cavity containing the $PbO_2$ was filled with about 30 milliliters of 30% $H_2SO_4$, standard lean-acid battery electrolyte. The Zn electrode anode cavity was filled with about 30 milliliters of 30% KOH solution. This electrochemical cell was cycled between charging and discharging over a period of several weeks.

The overall chemical reactions for the cell were:

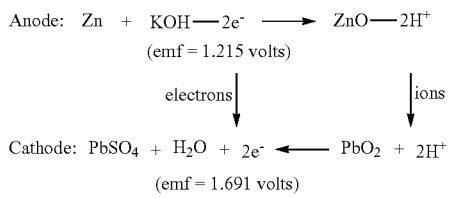

Electromotive force (emf) was referenced to a Standard Hydrogen Electrode (SHE).

Ions, i.e. protons, traveled inside the cell through the membrane. Electrons traveled outside the cell through the electrodes and external load circuit. The potentials added together across the cell with the direction of the reactions. Therefore, the theoretical (no load) cell potential $V_c$ was about 2.9 volts.

The cell was charged for about 4 hours at 200 milliamps at which point the open circuit potential $V_{oc}$ was measured at 2.92 volts. The cell was discharged through a load at about 0.2 amps (200 milliamps) for 0.5 hour, while the potential under load fell from 2.48 to 1.74 volts. The cell was allowed to stand for a week and then recharged for about 4 hours at 150 milliamps and discharged again at 0.2 amps from 2.25 to 1.36 volts. After another week, the cell was cycled, following a similar charging and discharging.

This result was compared with conventional cells in which the zinc electrode has been employed (silver-zinc, nickel-zinc) generally show discharge potentials of 1.5 to 1.6 volts.

EXAMPLE 1d

Following Example 1c, a white residue was noticed. The cell was disassembled and a pinhole size leak was observed in the membrane. The white residue was attributed to $K_2SO_4$ formed from mixed electrolyte, ending the electrochemical reaction.

This demonstrated that a micro-porous membrane would not have successfully function to separate the two half cells.

EXAMPLE 2a

A membrane was made following the procedure of Example 1a. The procedure was modified only in the use of 0.3 grams of poly(acrylic acid) having a molecular weight of 1,200,000 (Carbopol® 980). The poly(acrylic acid) was added to 5.0 grams of polyisobutylene.

EXAMPLE 2b

According to the invention a cell was made with the configuration: $MnO/H_2SO_4/KOH/Zn$. The electrochemical cell was made by clamping together two cell cavities separated by the membrane of Example 2a. The cathode cell cavity contained a positive manganese(II) (MnO) electrode. The anode cell cavity contained the zinc electrode of Example 1c. The electrode dimensions were about 4.5 centimeters×6.5 centimeters.

The MnO cathode was fabricated from MnO powder (ALFA Inorganics, Inc., Beverly, Mass.). Several grams of the MnO powder were mixed with ethylene glycol to form a paste and applied to a sintered fiber nickel substrate (INCO Specialty Products, Mississauga, Ontario, Canada).

For this system the half cell potential for the Zn anode side was about 1.215 volts and for the Mn cathode side was about 0.8 volts. The overall theoretical potential difference approached 2.02 volts.

The membrane was hydrated with aqueous electrolytes. The cell cavities were filled with the electrolytes as in Example 1c. The cell was connected to a strip chart recorder to record charging and discharging. The cell was charged at 50 milliamps for about 12 hours. The open circuit potential was measured at 2.35 volts. The initial high open circuit potential was attributed to charging the electrolyte. A load was applied to the cell producing a current of about 22 milliamps. The cell potential under load initially was 1.8 volts, decreased to 1.65 volts after 5 minutes, decreased to 1.55 volts after 10 minutes, and decreased to 1.2 volts after 30 minutes.

The measurements from the MnO/Zn cell of this Example 2b were compared to the measurements from the $PbO_2$/Zn cell of Example 1c. The range of discharge of potential for these cells is normally about 1.4 to 1.0 volts. In contrast, the electrochemical cell of the invention produced a measurably higher potential through most of the discharge time period. Since the cell energy density and power delivered are proportional to the square of the voltage, the increase in voltage was noteworthy.

EXAMPLE 2c

It was noticed that the nickel current collector substrate of the MnO electrode had corroded. This was attributed to the sintered fiber nickel substrate. A different MnO electrode was fabricated to replace the corroded electrode. $PbO_2$ was scraped off of a commercial electrode to expose a lead grid substrate. A mixture consisting of 3.8 grams Mn(II)O powder, 1.0 grams ethyl cellulose (Sigma Chemical Co. St. Louis, Mo. 53178) and 0.2 grams Pyrograf® III (Pyrograf Products, Inc., Cedarville, Ohio 45314) carbon nano-fiber was prepared. A paste was made of the powders with small quantities of ethanol and THF solvents. The paste was applied to the lead grid and dried. This Mn(II)O cathode was wrapped in a layer of Permion 2291 40/20 permeable graft copolymer membrane battery separator. A Zn anode similar to that described in Example 1c was also wrapped in a layer of Permion 2291 40/20 permeable membrane battery separator. Each electrode was installed in a cell cavity as in Example 1c. A piece of the membrane used in Example 1a was clamped between the cell cavity halves. The Mn and Zn electrode cavities were filled with the aqueous $H_2SO_4$ and KOH electrolytes as in Example 1c.

The cell was charged for about 5 hours at 100 milliamps. Immediately after charging, the open circuit potential was measured at about 2.48 volts. A 22 milliamps discharge current was drawn from the cell for about 1 hour 15 minutes. The cell potential under load was initially about 2.3 volts, 2.0 volts after 20 minutes, 1.6 volts after 40 minutes, 1.3 volts after 60 minutes, and 1 volt after 75 minutes. This data was plotted and labeled Discharge #1 in FIG. 1.

The cell was recharged at 200 milliamps for 5 hours and discharged at 22 milliamps. The initial potential under load was about 2.34 volts. This dropped to 2.2 volts after 20 minutes, 2.1 volts after 40 minutes, 1.95 volts after 60 minutes, 1.8 volts after 80 minutes, 1.3 volts after 120 minutes, and finally 1.0 volt at about 140 minutes. This data was plotted and labeled Discharge #2 in FIG. 1.

The cell was recharged, this time at 200 milliamps for about 5 hours. It was discharged at 22 milliamps with an initial potential under load of about 2.31 volts. The potential decreased to about 2.2 volts after 20 minutes, 2.15 after 40 minutes, 1.95 volts after 60 minutes, 1.8 volts after 80 minutes, 1.6 volts after 120 minutes, 1.3 volts after 160 minutes, and finally about 1.05 volts after 200 minutes. This data was plotted and labeled Discharge #3 in FIG. 1.

These cell cycles demonstrated the increased potential discharge capability of the cell of the invention compared with that of a conventional Mn—Zn alkaline cell. The measurements of the first discharge of a rechargeable commercial Mn/Zn AA cell were plotted in FIG. 1 for comparison.

EXAMPLE 2d

Comparative

Example 1a was repeated with the addition of more than 6 wt % poly(acrylic acid). It was observed that a small increase in the amount of poly(acrylic acid) over 6 wt % significantly altered the physical integrity of the membrane. After solvent removal, the membrane had a Swiss cheese pattern of randomly distributed holes through it. The membrane was unsuitable for separating electrolytes in an electrochemical cell.

A uniform, integral membrane could not be produced with a proportion of poly(acrylic acid) of greater than about 6 wt % by the method of the invention.

EXAMPLE 3

The Zn anode of Example 2c was replaced. A commercial PbO anode was paired with the Mn(II)O cathode of Example 2c. A piece of the membrane fabricated in Example 1a was used and hydrated with aqueous electrolytes. As in Example 1c, the anode cavity was filled with aqueous KOH. The cathode cavity was filled with aqueous $H_2SO_4$. The cell configuration was: $MnO/H_2SO_4/KOH/PbO$.

The net half cell reactions were the following:

$$PbO+H_2O+2e^- \leftrightarrow Pb+2OH^-$$

(emf=−0.58 volts vs. standard hydrogen electrode SHE)

$$MnO_2-2e^- \leftrightarrow MnO^{-2}+2H_2O-4OH^-$$

(emf=0.60 volts vs. standard hydrogen electrode SHE)

Figure 2:
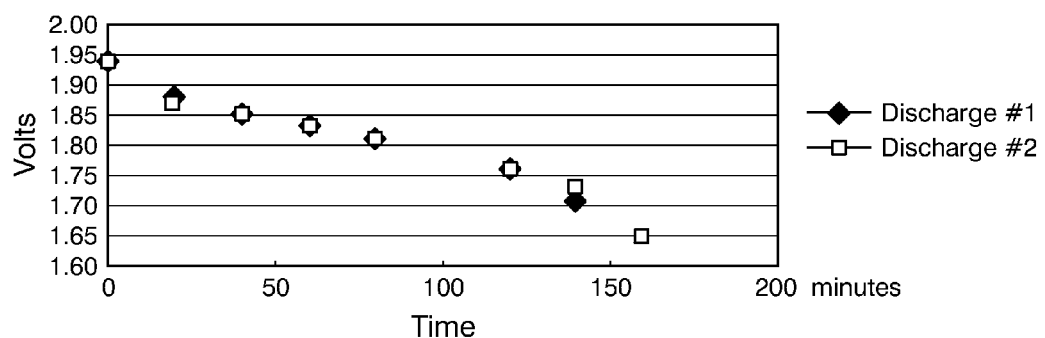
FIG. 2 is a plot of data demonstrating a Mn/PbO cell of the invention by way of two voltage discharges with respect to time.

The cell was charged at 200 milliamps for 5 hours. The open circuit potential of about 2.03 volts was measured. A load of 22 milliamps was applied to the cell. The initial potential was 1.94 volts, decreasing to 1.88 volts after 20 minutes, 1.85 volts after 40 minutes, 1.83 volts after 60 minutes, 1.82 volts after 80 minutes, about 1.79 volts after 100 minutes, 1.76 volts after 120 minutes, and finally 1.71 volts after 140 minutes. This data was plotted and labeled Discharge #1 in FIG. 2.

The cell was recharged again the following day at 200 milliamps for 5 hours. Again, an open circuit potential of about 2.02 volts was recorded. The cell was discharged at 22 milliamps. The initial potential was 1.94 volts, decreasing to 1.87 volts after 20 minutes, 1.85 volts after 40 minutes, 1.83 volts after 60 minutes, 1.81 volts after 80 minutes, 1.78 volts after 100 minutes, 1.76 volts after 120 minutes, 1.73 volts after 140 minutes, about 1.65 volts after 160 minutes, and finally 1.59 volts after 180 minutes. This data was plotted and labeled Discharge #2 in FIG. 2.

The negative half cell reaction of the PbO electrode was found to be reasonably reversible.

EXAMPLE 4

Comparative

Example 1a was repeated. However, amounts of poly(acrylic acid) well in excess of 0.3 grams were added to 5.0 grams of polyisobutylene in the attempt to produce a membrane with about 15 wt % to 20 wt % poly(acrylic acid). As solvent was removed from the membrane on the casting surface, holes formed. The membrane could not be lifted from the casting surface in a single piece so membrane pieces were removed. Membrane pieces were observed to be lacking in strength when stretched manually. It was concluded that membranes could not be successfully made with these proportions of poly(acrylic acid).

EXAMPLE 5

Comparative

A membrane was formed according to Example 1a; however, it appeared to be thinner than 0.1 millimeters. An attempt was made to remove the membrane from the casting surface scraping with a razor blade. Scraping deformed the membrane into accordion folds. The membrane was tested by hand. Stretching caused holes to form. The membrane broke easily and judged to be not strong. The membrane was rejected for testing in a cell for apparent lack of strength and ease of hole formation.

The accordion folding may have been reduced or avoided with the addition of more mineral oil to the casting plate. This was not tried because of the apparent lack of strength of the membrane.

EXAMPLE 6

Comparative

It was estimated that a polyisobutylene-poly(acrylic acid) polymer membrane comprising less than 4 wt % poly(acrylic acid) would not have enough conductivity to produce an energy density that would make it useful in an electrochemical cell.

EXAMPLE 7

Comparative

A film was cast with a wet solution mixture. Solvent was removed, but a membrane did not form. The gelatinous mass on the casting surface appeared to be a hydrogel.

The foregoing discussion discloses and describes embodiments of the invention by way of example. One skilled in the art will readily recognize from this discussion, that various changes, modifications and variations can be made therein without departing from the spirit and scope of the invention as defined in the following claims.

What is claimed is:

1. An electrochemical cell comprising an ion permeable, liquid and vapor impermeable, membrane made by the method of:
   a. dissolving high molecular weight polyisobutylene polymer having an average molecular weight of at least about 80,000 in a dry first solvent to produce a first solution;
   b. dissolving poly(acrylic acid) polymer having a molecular weight of at least about 100,000 in a dry second solvent and neutralizing to form a second solution;
   c. mixing the first solution with the second solution to form a solution mixture comprising about 4 wt % to about 6 wt poly(acrylic acid) polymer based on polymers in the solution mixture;
   d. casting a film of the solution mixture on a casting surface and removing the first solvent and second solvent;
   e. thereby forming an ion permeable, liquid and vapor impermeable, membrane having a thickness of about 0.1 millimeters or greater.

2. The electrochemical cell comprising the ion permeable membrane made by the method of claim 1, wherein the ion Impermeable membrane has a thickness of 0.1 millimeters to 0.4 millimeters.

3. The electrochemical cell comprising the ion permeable membrane made by the method of claim 1, wherein the high molecular weight polyisobutylene polymer has a molecular weight of about 100,000 to about 1,000,000.

4. The electrochemical cell comprising the ion permeable membrane made by the method of claim 1, wherein the poly(acrylic acid) polymer has a molecular weight of about 1.2 million to about 4 million.

5. The electrochemical cell comprising the ion permeable membrane made by the method of claim 1, wherein the poly(acrylic acid) polymer comprises about 4 wt % to about 5.7 wt % of the polymer in the solution mixture.

6. The electrochemical cell comprising the ion permeable membrane made by the method of claim 1, additionally comprising:
   removing the ion permeable membrane from the casting surface and hydrating.

7. The electrochemical cell comprising the ion permeable membrane made by the method of claim 1, wherein the first solvent is selected from the group consisting of tetrahydrofuran (THF) and dichloro methane.

8. The electrochemical cell comprising the ion permeable membrane made by the method of claim 1, wherein the second solvent is selected from the group consisting of methyl alcohol, ethyl alcohol, propyl alcohol, isopropyl alcohol, butyl alcohol, isobutyl alcohol and isobutyl alcohol.

9. The electrochemical cell comprising the ion permeable membrane made by the method of claim 1, wherein the first solvent is tetrahydrofuran (THF) and the second solvent is ethyl alcohol.

10. The electrochemical cell comprising the ion permeable membrane made by the method of claim 1, wherein the membrane is in contact with an anode cell electrolyte and a cathode cell electrolyte on opposing faces.

11. An ion permeable, liquid and vapor impermeable, membrane made by the method of:
   a. dissolving high molecular weight polyisobutylene polymer having an average molecular weight of at least about 80,000 in a dry first solvent to produce a first solution;
   b. dissolving poly(acrylic acid) polymer having a molecular weight of at least about 1.2 million in a dry second solvent and neutralizing to form a second solution;
   c. mixing the first solution with the second solution to form a solution mixture comprising about 4 wt % to about 6 wt % poly(acrylic acid) polymer based on the polymers in the solution mixture, the solution mixture having a viscosity of about 5 centipoise to about 1000 centipoise;
   d. casting a film of the solution mixture on a casting surface and removing the first solvent and second solvent;
   e. thereby forming an ion permeable, liquid and vapor impermeable, membrane having a thickness of 0.1 mm or greater.

12. The ion permeable, liquid and vapor impermeable, membrane made by the method of claim 11, wherein the ion permeable membrane has a thickness of 0.1 millimeters to 0.4 millimeters.

13. The ion permeable, liquid and vapor impermeable, membrane made by the method of claim 11, wherein the high molecular weight polyisobutylene polymer has a molecular weight of about 100,000 to about 1,000,000.

14. The ion permeable, liquid and vapor impermeable, membrane made by the method of claim 11, wherein the poly(acrylic acid) polymer has a molecular weight of about 1.2 million to about 4 million.

15. The ion permeable, liquid and vapor impermeable, membrane made by the method of claim 11, wherein the poly(acrylic acid) polymer comprises about 4 wt % to about 5.7 wt % of the polymer in the solution mixture.

16. The ion permeable, liquid and vapor impermeable, membrane made by the method of claim 11, wherein the poly(acrylic acid) polymer comprises about 4 wt % to about 5 wt % of the polymer in the solution mixture.

17. The ion permeable, liquid and vapor impermeable, membrane made by the method of claim 11, additionally comprising:
   removing the ion permeable membrane from the casting surface and hydrating.

18. The ion permeable, liquid and vapor impermeable, membrane made by the method of claim 11, wherein the first solvent is selected from the group consisting of tetrahydrofuran (THF) and dichloro methane.

19. The ion permeable, liquid and vapor impermeable, membrane made by the method of claim 11, wherein the second solvent is selected from the group consisting of methyl alcohol, ethyl alcohol, propyl alcohol, isopropyl alcohol, butyl alcohol, isobutyl alcohol and isobutyl alcohol.

20. The ion permeable, liquid and vapor impermeable, membrane made by the method of claim 11, wherein the first solvent is tetrahydrofuran (THF) and the second solvent is ethyl alcohol.

* * * * *